(12) United States Patent
Pratt (10) Patent No.: US 7,255,435 B2
(45) Date of Patent: Aug. 14, 2007

(54) BLUE BLOCKING TENS

(76) Inventor: Steven G. Pratt, 9850 Genesee Ave., Suite 310, La Jolla, CA (US) 92307

( * ) Notice: Subject to any disclaimer, the term of this patent is extended or adjusted under 35 U.S.C. 154(b) by 393 days.

(21) Appl. No.: 10/899,463

(22) Filed: Jul. 26, 2004

(65) Prior Publication Data

US 2005/0043793 A1  Feb. 24, 2005

Related U.S. Application Data (63) Continuation-in-part of application No. 10/423,173, filed on Apr. 25, 2003, now Pat. No. 6,955,430.

(51) Int. Cl.
G02C 7/10 (2006.01)
(52) U.S. Cl. ......................... 351/44; 351/163
(58) Field of Classification Search ................. 351/44, 351/41, 163, 177
See application file for complete search history.

(56) References Cited

U.S. PATENT DOCUMENTS

| | | |
|---|---|---|
| 1,332,410 A | 3/1920 | Potts |
| 1,354,040 A | 9/1920 | Hammon |
| 1,536,828 A | 5/1925 | Drescher |
| 1,619,341 A | 3/1927 | Gagnon |
| 1,697,030 A | 1/1929 | Tillyer |
| 1,741,536 A | 12/1929 | Rayton |
| 1,910,466 A | 5/1933 | Glancy |
| 1,942,400 A | 1/1934 | Glancy |
| 2,406,608 A | 8/1946 | Joyne |
| 2,442,849 A | 6/1948 | Glazer |
| 3,229,303 A | 1/1966 | Jonassen |
| 4,515,448 A | 5/1985 | Tackles |
| 4,613,217 A | 9/1986 | Fuerter et al. |
| 4,741,611 A | 5/1988 | Burns |
| 4,761,315 A | 8/1988 | Logan et al. |
| 4,859,048 A | 8/1989 | Jannard |
| 4,867,550 A | 9/1989 | Jannard |
| 4,878,748 A | 11/1989 | Johansen et al. |
| 4,952,046 A | 8/1990 | Stephen et al. |
| 5,050,979 A | 9/1991 | Shinohara |
| 5,050,980 A | 9/1991 | Shinohara |
| 5,208,614 A | 5/1993 | Jannard |
| 5,400,175 A | 3/1995 | Johansen et al. |
| 5,555,038 A | 9/1996 | Conway |
| 5,648,832 A | 7/1997 | Houston et al. |
| 5,662,707 A | 9/1997 | Jinkerson |

(Continued)

Primary Examiner—Hung Xuan Dang
(74) Attorney, Agent, or Firm—Stetina Brunda Garred & Brucker (57) ABSTRACT

An article of an eye wear worn externally upon an eye, having an article which article comprises a wavelength transmission blocker. The wavelength transmission blocker has a lutein assimilated therein for preventing radical damage in the eye. The wavelength transmission blocker is sized and configured to maximize visual acuity and block at least 80% of light wavelengths throughout a blue light spectrum set in a range from about 400 nm to about 510 nm. Preferably, the wavelength transmission blocker is operative to block substantially 100% of light wavelengths lower than 420 nm, and to block about 99% light wavelength at 420 nm and about 20% of light wavelength at 510 nm. Preferably, the wavelength transmission blocker blocks a gradually reduced percentage of light wavelengths between 420 nm to 510 nm. The wavelength transmission blocker is also operative to block a portion of light wavelengths between 510 nm to 650 nm.

37 Claims, 6 Drawing Sheets

U.S. PATENT DOCUMENTS 5,774,201 A 6/1998 Tackles
6,787,147 B1 * 9/2004 Huner et al. ............. 424/401
6,955,430 B2 * 10/2005 Pratt ............. 351/44

* cited by examiner

| SPECTRAL TRANSMITTANCE | | | |
|---|---|---|---|
| 280nm | -0.002% | 535nm | 22.227% |
| 285nm | -0.001% | 540nm | 22.894% |
| 290nm | -0.002% | 545nm | 23.554% |
| 295nm | 0% | 550nm | 23.956% |
| 300nm | 0.001% | 555nm | 24.076% |
| 305nm | -0.004% | 560nm | 23.919% |
| 310nm | 0% | 565nm | 23.651% |
| 315nm | 0% | 570nm | 23.506% |
| 320nm | -0.001% | 575nm | 23.716% |
| 325nm | -0.002% | 580nm | 24.199% |
| 330nm | -0.002% | 585nm | 24.738% |
| 335nm | -0.003% | 590nm | 25.121% |
| 340nm | 0.001% | 595nm | 25.275% |
| 345nm | 0.003% | 600nm | 25.247% |
| 350nm | 0.001% | 605nm | 25.191% |
| 355nm | 0.001% | 610nm | 25.134% |
| 360nm | 0% | 615nm | 25.082% |
| 365nm | -0.001% | 620nm | 25.006% |
| 370nm | 0% | 625nm | 24.876% |
| 375nm | 0.003% | 630nm | 24.693% |
| 380nm | 0.005% | 635nm | 24.516% |
| 385nm | 0.015% | 640nm | 24.42% |
| 390nm | 0.005% | 645nm | 24.503% |
| 395nm | -0.004% | 650nm | 24.876% |
| 400nm | -0.003% | 655nm | 25.551% |
| 405nm | 0.003% | 660nm | 26.599% |
| 410nm | 0.065% | 665nm | 28.067% |
| 415nm | 0.276% | 670nm | 29.886% |
| 420nm | 0.599% | 675nm | 32.076% |
| 425nm | 0.977% | 680nm | 34.514% |
| 430nm | 1.412% | 685nm | 37.204% |
| 435nm | 1.945% | 690nm | 39.935% |
| 440nm | 2.632% | 695nm | 42.743% |
| 445nm | 3.496% | 700nm | 45.427% |
| 450nm | 4.55% | 705nm | 48.035% |
| 455nm | 5.717% | 710nm | 50.405% |
| 460nm | 6.906% | 715nm | 52.662% |
| 465nm | 8.189% | 720nm | 54.592% |
| 470nm | 9.505% | 725nm | 56.362% |
| 475nm | 10.87% | 730nm | 57.876% |
| 480nm | 12.218% | 735nm | 59.139% |
| 485nm | 13.527% | 740nm | 60.328% |
| 490nm | 14.475% | 745nm | 61.637% |
| 495nm | 15.909% | 750nm | 62.339% |
| 500nm | 17.079% | 755nm | 62.792% |
| 505nm | 18.26% | 760nm | 63.22% |
| 510nm | 19.372% | 765nm | 63.591% |
| 515nm | 20.279% | 770nm | 63.928% |
| 520nm | 20.901% | 775nm | 64.186% |
| 525nm | 21.308% | 780nm | 64.405% |
| 530nm | 21.673% | | |

BLUE BLOCKING TENS

CROSS-REFERENCE TO RELATED APPLICATIONS

This application is a continuation-in-part of application Ser. No. 10/014,298 filed Dec. 11, 2001 and application Ser. No. 10/423,173 filed Apr. 25, 2003, which are incorporated herein in their entireties by reference.

STATEMENT RE: FEDERALLY SPONSORED RESEARCH/DEVELOPMENT

Not Apllicable

BACKGROUND OF THE INVENTION

The present invention relates generally to optical lenses, and more particularly to externally-worn optical lenses which are designed to minimize glare, contrast sensitivity, chromatic and spherical aberrations and color distortion while maximizing visual acuity and blockage of a predetermined percentage of light wavelength transmission throughout the blue light spectrum.

The incidence of cataracts and macular degeneration is increasing worldwide. Causes for this condition range from atmospheric ozone depletion, which increases exposure to damaging electromagnetic radiation, to exposure to violet and blue light wavelengths, ultraviolet A and B wavelengths, and infrared wavelengths, all of which damage vulnerable eye components. A specific potentially dangerous situation occurs where a synthetic intraocular lens implant is surgically placed in the eye of a patient after removal of the crystalline lens. In particular, as the human lens ages, it is subject to nuclear sclerosis, known as "brunescent cataract," which, because of its color, blocks at least a portion of blue light entry generally up to 450 nm. In fact, human studies show that a normal 53 year old crystalline lens transmits only 10-50 percent of visible blue light to the retina. Because this blue light can be quite damaging to the retina, such natural blockage is highly desired. If this natural lens becomes generally inoperative because of critical cataract growth, it typically is surgically replaced within a lens implant. Present lenses employed for implant, however, do not block wavelengths above 400 nm, thus resulting in 100% passage of blue light (400 nm to 510 nm) to the retina and resulting retina exposure to potential hazard.

In view of the retinal hazard caused by wavelength transmission through such an implanted lens, it is apparent that a need is present for intraocular protection against damaging blue light hazards, with such protection extending to blockage of ultraviolet and infrared wavelength transmissions as advisable. Accordingly, the primary object of the present invention is to provide an implantable synthetic replacement lens wherein such a lens blocks at least a significant portion the wavelength transmission between about 400 and 510 nm.

Another object of the present invention is to provide an implantable synthetic replacement lens wherein, in addition to blocking a significant portion thereof of visible wavelength transmission between about 400 and 510 nm, the lens blocks ultraviolet A and B and infrared wavelength transmissions.

Yet another object of the present invention is to provide methodology whereby a patient is provided with protection from ocularly damaging wavelength transmission by implantation of a synthetic intraocular refractive lens.

In addition, many people wear external eye wear, such as eyeglasses, sunglasses, goggles and contact lenses. Typically, these types of external eye wear provide inadequate blue-blocking protection for the eye. For example, although sunglasses and goggles are often polarized to block some light, they do not adequately block wavelength transmission between 400 and 510 nm, ultraviolet A and B, and infrared wavelength transmission. Adding such protection could advantageously allow a wearer to selectively protect their eyes, or remove the eyewear when blocking of such light is hazardous. Therefore, it is an object of the present invention to extend this type of protection to all forms of external eye wear.

These and other objects of the present invention will become apparent through the description thereof which now follows.

BRIEF SUMMARY OF THE INVENTION

In response to the above-noted needs, there is herein disclosed an article of externally-worn eye wear which is designed to minimize glare, contrast sensitivity, chromatic and spherical aberrations and color distortion while maximizing visual acuity and blockage of light wavelength transmission throughout the blue light spectrum. More specifically, this specified eye wear has a wavelength transmission blocker for blocking a significant portion of the transmission of light wavelengths between 400 nm and 510 nm, while still passes the ANSI Z80.3-2001 standard. For example, the wavelength transmission blocker is incorporated within eyeglasses, sunglasses, goggles, or contact lenses, but it is contemplated that the present invention could be applied to any eye wear that is worn externally to the eyeball. In one embodiment, the wavelength transmission blocker also blocks ultraviolet A wavelengths, ultraviolet B wavelengths, infrared wavelengths, and combinations thereof. The wavelength transmission blocker can be a tint composition disposed exteriorly upon the lens, or it can be a tint composition disposed interiorly within the lens.

The eye wear advantageously reduces eye damage caused by the blocked light. Also, since the eye wear is exteriorly worn, the user can selectively choose to wear the eye wear and protect their eyes, or the user can selectively choose to remove the eye wear if blockage of the light could cause other hazards.

In one embodiment, the eye wear worn externally upon an eye includes an article which article comprises a wavelength transmission blocker. The wavelength transmission blocker has a lutein assimilated therein for preventing radical damage in the eye. The wavelength transmission blocker is sized and configured to maximize visual acuity and block at least 80% of light wavelengths throughout a blue light spectrum set in a range from about 400 nm to about 510 nm. Preferably, the wavelength transmission blocker is operative to block substantially 100% of light wavelengths lower than 420 nm, and to block about 99% light wavelength at 420 nm and about 20% of light wavelength at 510 nm. In one embodiment, the wavelength transmission blocker blocks a gradually reduced percentage of light wavelengths between 400 nm to 510 nm. The wavelength transmission blocker is also operative to block a portion of light wavelengths between 510 nm to 650 nm.

The eye wear is selected from a group consisting of eyeglasses, sunglasses, goggles and contact lenses. The wavelength transmission blocker is also operative to block wavelength transmission of wavelengths chosen from a group consisting of ultraviolet A wavelengths, ultraviolet B wavelengths, infrared wavelengths, and combination thereof. The wavelength transmission blocker includes a tint composition. The article comprises a lens and a tint composition disposed exteriorly upon the lens or interiorly within the lens.

In another embodiment, an article of eye wear is provided. The article comprises a wavelength transmission blocker sized and configured to block predetermined percentages of light transmission at selective wavelengths. The predetermined percentages are substantially 100% at wavelengths up to 400 nm; and gradually reduced from about 99.3% at wavelength of 405 nm to about 80.6% at wavelength of 510 nm. Preferably, the wavelength transmission blocker includes a lutein assimilated therein. Preferably but optionally, the predetermined percentages further include 80% to 70% at wavelengths of 510 nm and 650 nm. The eye wear includes a pair of eyeglasses, sunglasses or contact lenses, or a surgically implantable synthetic intraocular lens, for example. The wavelength transmission blocker is preferably operative to block ultraviolet A wavelengths, ultraviolet B wavelengths, infrared wavelengths, and combinations thereof. The wavelength transmission blocker is a tint composition in one embodiment.

BRIEF DESCRIPTION OF THE DRAWINGS

These as well as other features of the present invention will become more apparent upon reference to the drawings wherein.

DETAILED DESCRIPTION OF THE INVENTION

Figure 1:
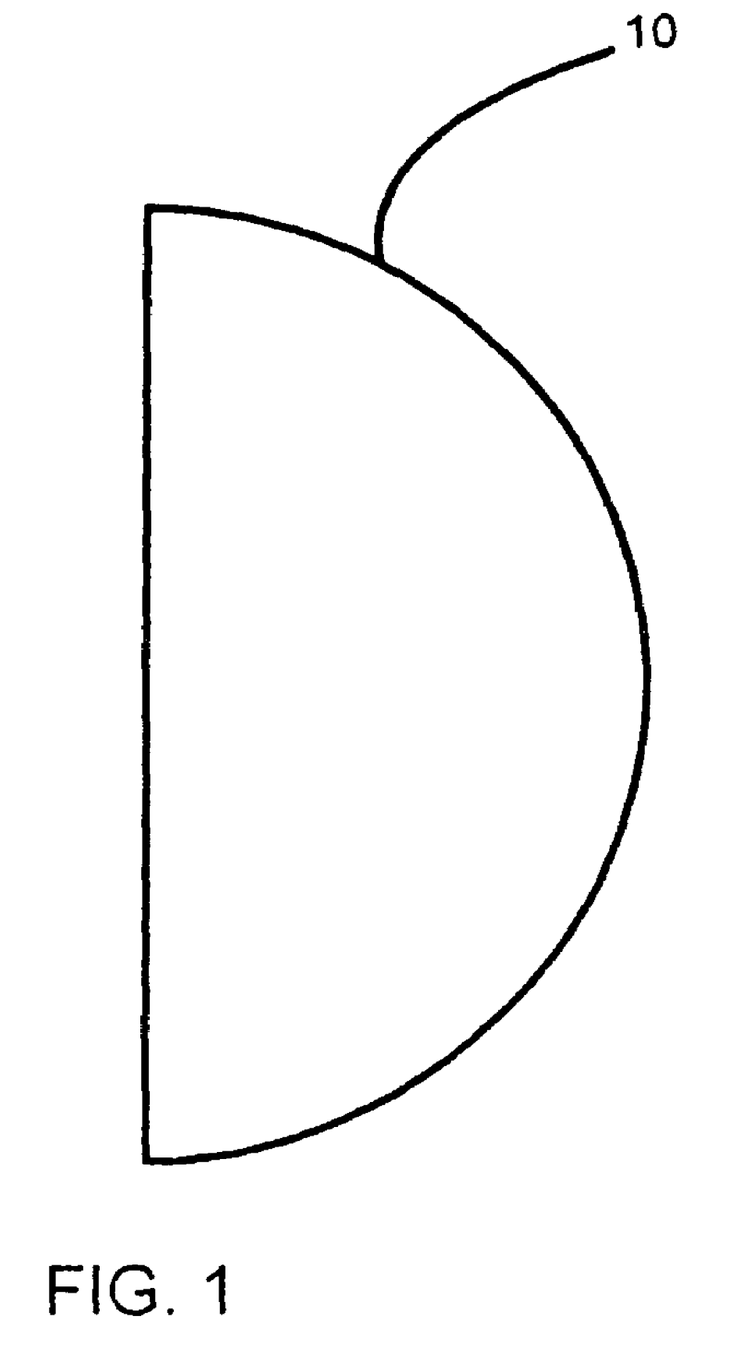
FIG. 1 is an enlarged side elevational view of a surgically implantable synthetic intraocular lens.

Referring now to drawings wherein the showings are for purposes of illustrating preferred embodiments of the present invention only, and not for purposes of limiting the same, FIG. 1 illustrates a surgically implantable synthetic intraocular lens 10 which is designed to minimize glare, contrast sensitivity, chromatic and spherical aberrations and color distortion while maximizing visual acuity and blockage of light wavelength transmission throughout the blue light spectrum. The lens 10 is surgically implanted as known in the art after removal of a diseased lens, or cataract, from the eye of a patient. Conversely, if the lens 10 is to be implanted without removal of the natural lens as indicated for correcting refractive errors, the lens 10, with necessary corrective attributes, is likewise implanted as known in the art. As earlier discussed, in addition to the danger associated with ultraviolet A, ultraviolet B, and infrared wavelengths, visible blue light (i.e., wavelengths above 400 nm) is now known to be potentially very dangerous to the retina component of an eye.

Consequently, in addition to blocking ultraviolet A and ultraviolet B wavelengths as well as infrared wavelengths, the lens 10 here illustrated blocks transmission therethrough of 100% of wavelengths up to 400 nm. The lens 10 also blocks light of wavelength range between 400 nm to 510 nm as much as possible, while still passes the ANSI Z80.3-2001 standard. In one embodiment, the lens 10 blocks wavelength range over 50% of wavelength range throughout the visible range, that is, from 400 nm to 710 nm shown in FIG. 6. Transmission prohibition is accomplished by a wavelength transmission blocker preferably being a tint composition provided as known in the art, either by exterior tinting procedures applied to each lens after lens formation, or by interiorly incorporating the tint composition within a blocking material from which a lens is subsequently derived. It should be noted herein that the wavelength transmission blocker of the present invention may be applied to various types of intraocular lenses known in the art through the utilization of such tinting methods. An exemplary intraocular lens 10 which may be advantageously subjected to the present wavelength transmission blocker is shown in U.S. Pat. No. 6,152,958, which is entitled "Foldable Thin Intraocular Membrane" and issued to Lee T. Nordan on Nov. 28, 2000.

Non-limiting tint composition products include those available from Brain Power, Inc., Miami, Fla., and from Phantom Tinting Co., San Diego, Calif. The lens 10 is constructed of bio compatible material, and typically will be injected molded or stamped from sheet stock and molded for direct placement into the eye. As would be apparent, should a physician not desire an implantable lens to include wavelength blockage other than at least a portion of visible blue light between about 400 and 510 nm, a tint composition can be employed that only blocks such visible blue wavelength transmission. The lens 10 is implanted through a conventional surgical procedure, and standard recovery time for the patient is experienced while retina well-being is thereby maintained.

Figure 6:
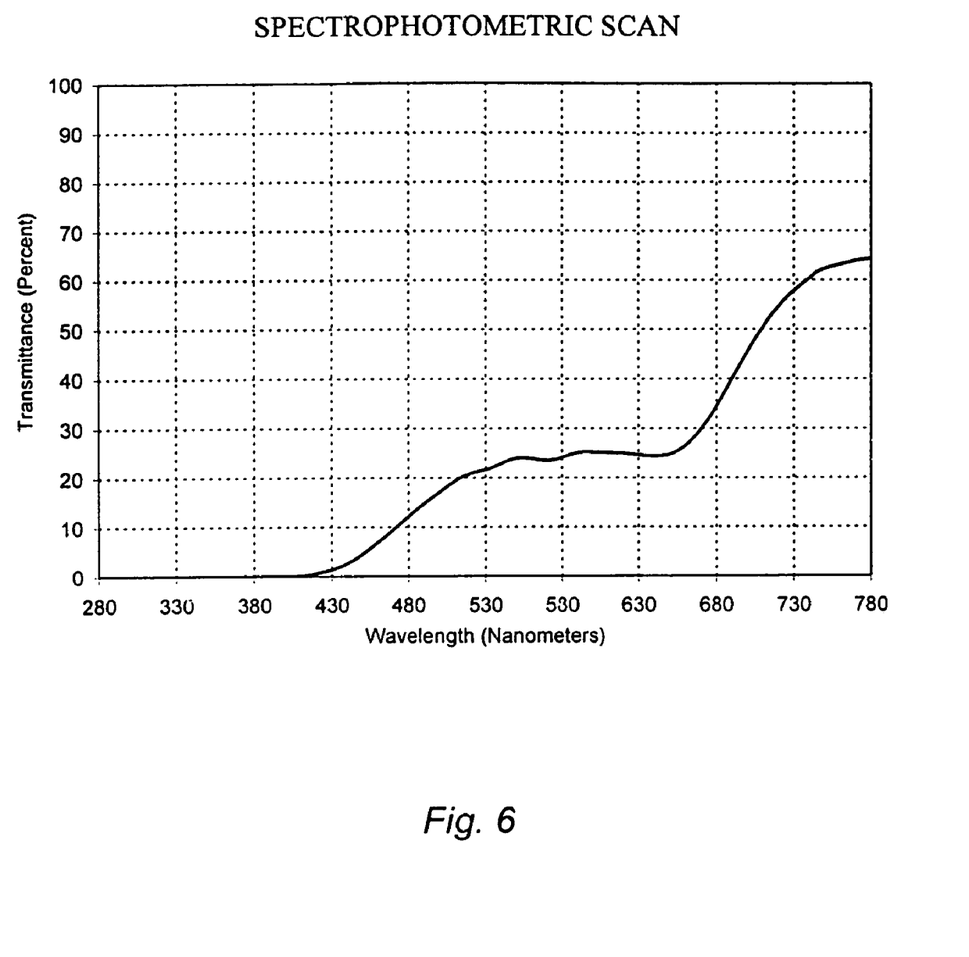
FIG. 6 is a graph illustrating the blockage of at least a portion of light wavelength transmission throughout the blue light spectrum.

Because total blue light blockage between 400 and 510 nm causes color distortion which, in turn, could create hazardous situations, such an inability to properly distinguish traffic device colors while driving, it is preferred that less than 100% blue light blockage occurs unless absolutely necessary for patient treatment. In the embodiment as illustrated in FIG. 6, the blockage for light up to about 400 nm is substantially 100%. As the wavelength increases, the blockage of the light reduces. For example, light blockage reduces from about 0% at 400 nm to about 80% at 510 nm. When the light intensity is strong or the patient's eyes are vulnerable to relatively strong visible light, it is preferable that the light throughout the visible range is also dimmed. Therefore, as shown in FIG. 6, about 75% of the light between 520 nm to 650 nm is blocked. The blockage is then gradually reduced to lower than 35% at 780 nm. It will be appreciated that the blocking percentage of light at wavelength range other than the blue light can be adjusted according to specific need of the patient. For example, the patient may selects to wear the lens with higher blocking percentage of the light between 520 nm to 650 nm under direct exposure of the sun and the lens with lower blocking percentage of the light between 520 nm to 650 nm in the environment when the light intensity is lower.

Turning now to FIGS. 2 through 5, a group of externally worn eye wear with a wavelength transmission blocker is illustrated. Unlike the implanted lens of FIG. 1, the eye wear depicted in FIGS. 2 through 5 is worn outside of the eye and can be selectively used to block potentially harmful blue light to thereby protect the eye.

Figure 2:
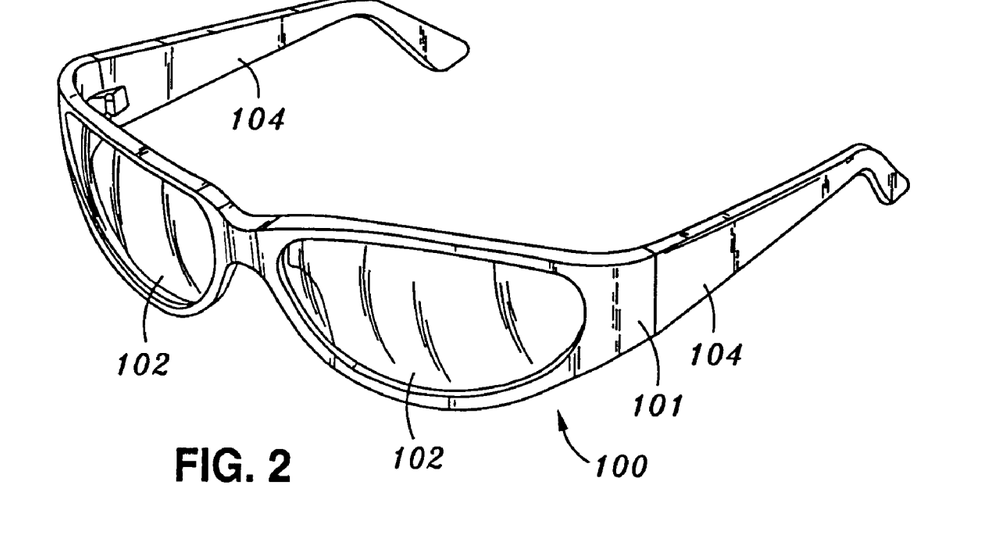
FIG. 2 is a side perspective view of a pair of eyeglasses with a wavelength transmission blocker.

FIG. 2 depicts a pair of eyeglass 100. As is known in the art, the eyeglasses 100 comprise a frame 101 with a pair of stems 104 disposed at opposing ends and extending therefrom. A pair of lenses 102 is disposed within the frames 101. The components are arranged such that the eye glasses 100 are supported by a user's ears and nose, and the lenses 102 are positioned in front of the user's eyes.

Figure 3:
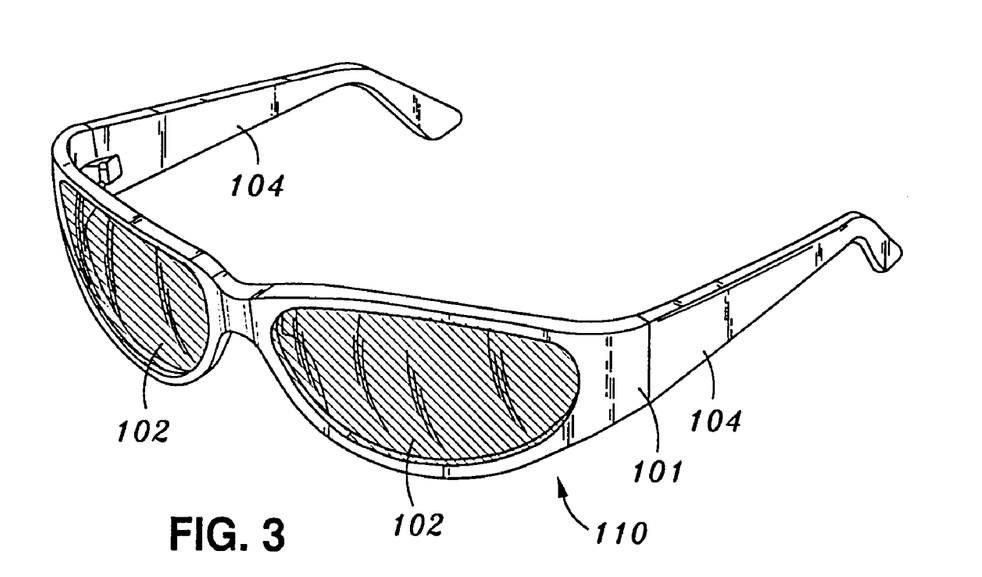
FIG. 3 is a side perspective view of a pair of sunglasses with a wavelength transmission blocker.

Similarly, FIG. 3 depicts a pair of sunglasses 110, which also include a pair of frames 101, stems 104 and lenses 102. The lenses 102 of the sunglasses 110 are typically polarized to thereby block harmful UV rays.

Figure 4:
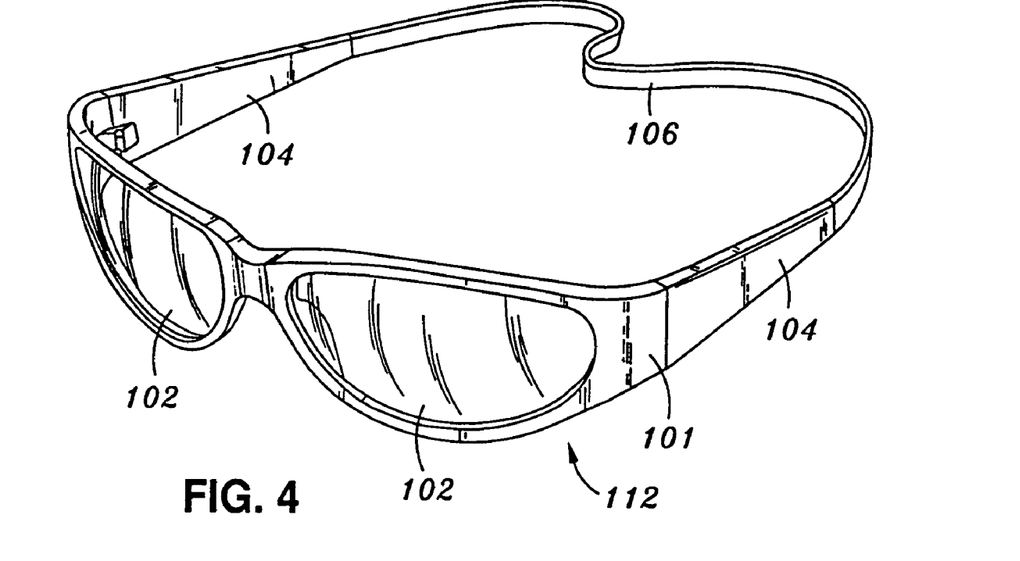
FIG. 4 is a side perspective view of a pair of goggles with a wavelength transmission blocker.

In addition, FIG. 4 depicts a pair of goggles 112. Like the eyeglasses 100 of FIG. 2 and the sunglasses 110 of FIG. 3, the goggles 112 as shown in FIG. 4 include a pair of frames 101, stems 104, and lenses 102. Extending between the stems 104 is a strap 106. The strap 106 is typically a flexible band, and a user stretches the strap 106 over the head. As such, the goggles 112 are supported by the user's nose, ears and the resiliency of the strap 106. The goggles 112 are typically worn in sporting events and other like activities, and the strap 106 retains the goggles 112 on the user's head. The lenses 102 can be of a plain variety and protect the user from objects entering the eye, or the lenses 102 can be of prescription type and allow the user to see clearly without the help of other corrective lenses.

Figure 5:
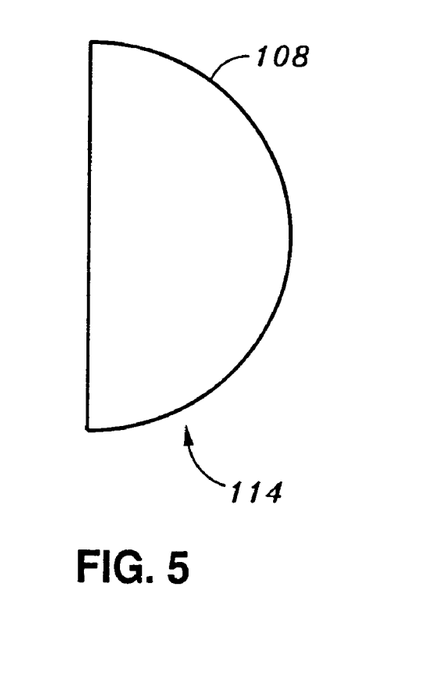
FIG. 5 is an enlarged side elevational view of a contact lens with a wavelength transmission blocker.

FIG. 5 depicts a contact lens 114, which is a well known corrective type lens that is worn directly on the exterior surface of the eye. The contact lens 114 comprises a lens 108 that is rounded to fit a particular user's eye. The lens 108 is made of a variety of different materials, but usually a polymeric material. It is envisioned that the contact lens 114 of FIG. 5 could be of a variety of types including, but not limited to, soft contact lenses, gas permeable contact lenses, daily disposable contact lenses or extended use contact lenses.

It is noted that the eye wear of FIGS. 2 through 5 each include a lens 102, 108. The lenses 102 of the eye wear of FIGS. 2 through 4 are disposed within frames 101 and thus positioned when worn. The lenses 108 of FIG. 5 are worn directly on the external surface of the eye. However, all of the lenses 102, 108 of FIGS. 2 through 5 are worn external to the eye.

Referring now to all the figures provided and mentioned herein, it is specifically contemplated that the wavelength transmission blocker of the present invention may simulate the functions of lutein. As is commonly understood in the art, lutein is a carotenoid which is mostly acquired in the body through eating certain fruits and green vegetables such as spinach. It is now believed through scientific findings that lutein appears to prevent free radical damage in the macula and retina, the two areas of the eye which are susceptible to cataracts and age-related macular degeneration. Because lutein acts as a natural sunshade against excess sunlight and is gradually lost in the eye with age, it is theorized that lutein loss may lead to retinal sun damage and ultimately to a degeneration in macular thickness. In this respect, simulation of lutein by the present wavelength transmission blocker would further protect the wearer against sunlight overexposure, and especially against undesirable blue light wavelengths in the range between 400 nm and 510 nm.

As noted above, the lenses 102, 108 of the embodiments shown in FIGS. 2 through 6 include a wavelength transmission blocker to thereby block transmission therethrough of a predetermined percentage of wavelengths between about 400 and 510 nm. Also, in one embodiment, the lenses 102, 108 block ultraviolet A and ultraviolet B wavelengths. The wavelength transmission blocker is preferably a tint composition provided as known in the art either by individual exterior tinting procedures applied to each lens 102, 108 after lens formation or by interiorly incorporating the tint composition into the lens 102, 108. Non-limiting tint composition products include those available from Brain Power, Inc., Miami, Fla., and from Phantom Tinting Co., San Diego, Calif. It should be contemplated herein that the preferred tint composition form of the present wavelength transmission blocker allows it to expand its applications to other settings and contexts such as a window of airplanes, automobiles, buildings and the like.

Figure 7:
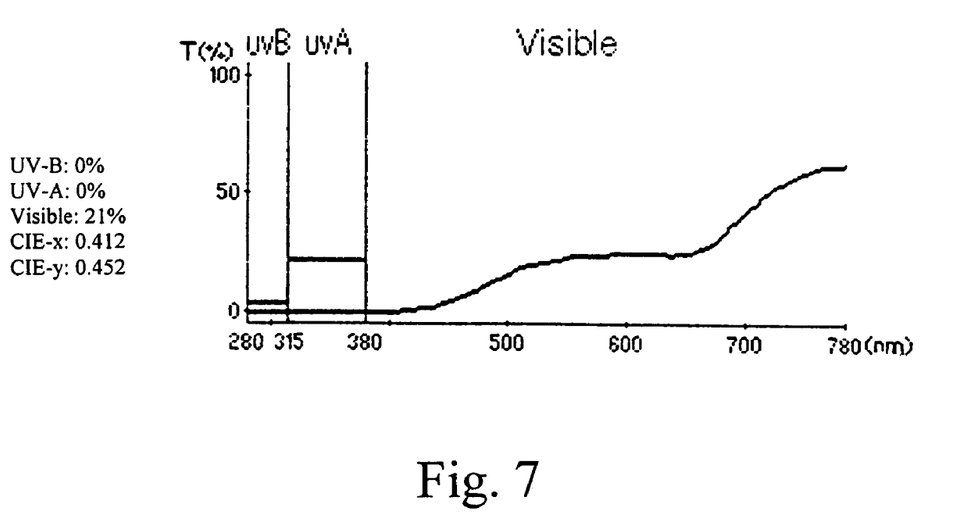
FIG. 7 shows the spectral response of a green tint which blocks a significant portion of blue light.
Figure 8:
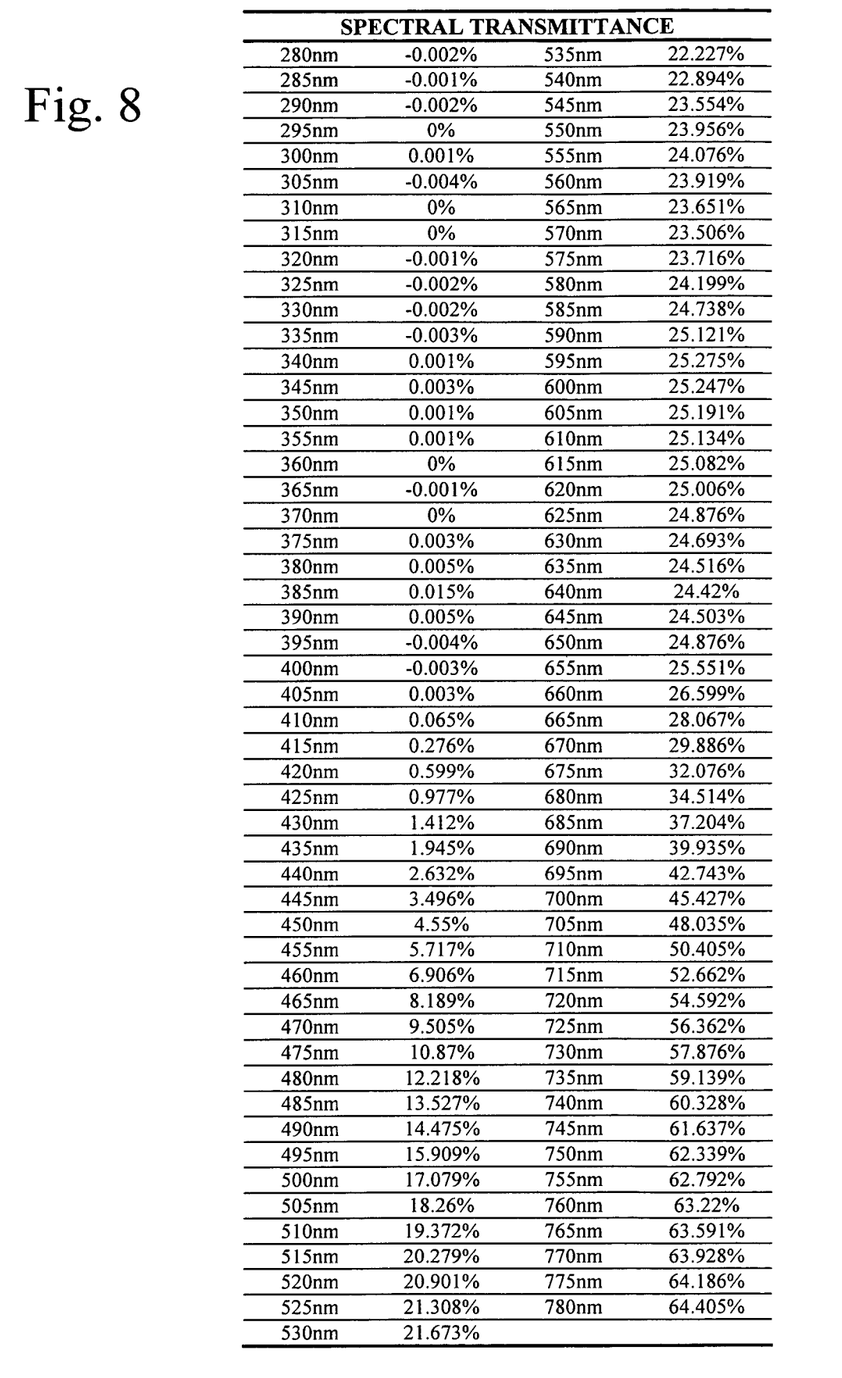
FIG. 8 is the empirical data of the spectral transmittance of FIGS. 6 and 7.

As discussed, the lens 102 or 108 may be tinted to selectively block the incident light at a specific wavelength. FIG. 7 shows a preferred green tint applied to the lens 102 or 108, and FIG. 8 is a table showing the spectral transmittance of the green tint as shown in FIG. 7. As shown, light at the ultraviolet A and B regions, that is, wavelengths from 280 nm to 315 nm and 315 nm to 380 nm, has substantial 0% of transmittance. In the blue region from 380 nm to 510 nm, a majority of light, such as more than 99% of the light, is also blocked to prevent the eyes from being damaged by the hazardous blue light. However, to avoid the hazardous situations, such an inability to properly distinguish traffic device colors while driving, less than 1% of the blue light between 400 nm and 510 nm is allowed to transmit through the lens 102 or 108. As the wavelength increases, the transmittance increases. A shown in FIGS. 7 and 8, the transmittances rises steeply from about 400 nm to about 530 nm and remains relatively flat in the region of 530 nm and 650 nm. Over 650 nm, the transmittance rises steeply again up to 780 nm.

Should a physician not desire the lens 102, 108 to include wavelength blockage other than at least a portion of visible blue light between about 400 and 510 nm, a tint composition can be employed that only blocks such visible blue wavelength transmission. Because total blue light blockage between 400 and 510 nm can cause color distortion, which in turn, could create unwanted situations such as an inability to properly distinguish traffic device colors while driving, it is preferred that less than 100% blue light blockage occurs unless absolutely necessary for the user. Instead, it is preferred that a portion up to about 20% of one or more of the blue light wavelengths between 400-510 nm be transmitted. Such transmission can be chosen to include a graduated percentage of various wavelength transmissions (e.g., 0% at 400 nm, 20% at 510 nm, etc.). Additionally but optionally, a percentage of the light transmission between 510 nm and 650 nm can also be blocked. The blocking percentage of the light transmission can be gradually reduced or constant of sum or all wavelengths between 510 and 650 nm.

As such, the externally worn eye wear of FIGS. 2 through 5 provide protective light blocking capability. In addition, since the eye wear can be removed as necessary, the eye wear allows for selective light blocking capability. In this respect, the wearer can use the eye wear when light blocking is non-hazardous to thereby protect the eye, and the user can remove the eye wear when light blocking might be hazardous.

This disclosure provides exemplary embodiments of the present invention. The scope of the present invention is not limited by the exemplary embodiments. Numerous variations, whether explicitly provided for by the specification or implied by the specification, such as variations in structure, dimension, type of material and manufacturing process may be implemented by one of skill in the art in view of the disclosure.

What is claimed is:

1. An article of eye wear worn externally upon an eye, the article comprising a wavelength transmission blocker having a lutein assimilated therein for preventing radical damage in the eye, the wavelength transmission blocker being sized and configured to maximize visual acuity and block at least 80% of light wavelengths throughout a blue light spectrum set in a range from about 400 nm to about 510 nm.

2. The article of claim 1, wherein the wavelength transmission blocker is operative to block substantially 100% of light wavelengths up to 400 nm.

3. The article of claim 1, wherein the wavelength transmission blocker is operative to block about 99% of light between 400 nm and 420 nm and about 20 of light at 510 nm.

4. The article of claim 1, wherein the wavelength transmission blocker is operative to block a gradually reduced percentage of light wavelengths between 400 nm to 510 nm.

5. The article of claim 1, wherein the wavelength transmission blocker is operative to block a portion of light wavelengths between 510 nm to 650 nm.

6. The article of claim 1, wherein the eye wear is selected from a group consisting of eyeglasses, sunglasses, goggles and contact lenses.

7. The article of claim 1, wherein the wavelength transmission blocker is operative to block wavelength transmission of wavelengths chosen from a group consisting of ultraviolet A wavelengths, ultraviolet B wavelengths, infrared wavelengths, and combination thereof.

8. The article of claim 1, wherein the wavelength transmission blocker is a tint composition.

9. The article of claim 1, wherein the article comprises a lens and a tint composition disposed exteriorly upon the lens.

10. The article of claim 1, wherein the article comprises a lens and a tint composition disposed interiorly within the lens.

11. An article of eye wear, comprising a wavelength transmission blocker being sized and configured to block predetermined percentages of light transmission at selective wavelengths, wherein the predetermined percentages being:
substantially 100% at wavelengths up to 400 nm; and
gradually reduced from about 99% at wavelength of 420 nm to about 80% at wavelength of 510 nm.

12. The article of claim 11, wherein the wavelength transmission blocker includes a lutein assimilated therein.

13. The article of claim 11, wherein the predetermined percentages are between 80% to 70% at wavelengths of 510 nm and 650 nm.

14. The article of claim 11, wherein the eye wear includes a pair of eyeglasses, sunglasses or contact lenses.

15. The article of claim 11, wherein the eye wear includes a surgically implantable synthetic intraocular lens.

16. The article of claim 11, wherein the wavelength transmission blocker is operative to block ultraviolet A wavelengths, ultraviolet B wavelengths, infrared wavelengths, and combinations thereof.

17. The article of claim 11, wherein the wavelength transmission blocker is a tint composition.

18. A semitransparent viewing surface, comprising a wavelength transmission blocker having a lutein assimilated therein for preventing radical damage in the eye, the wavelength transmission blocker being sized and configured to maximize visual acuity and block at least 80% of light wavelengths throughout a blue light spectrum set in a range from about 400 nm to about 510 nm.

19. The viewing surface of claim 18, wherein the viewing surface is a vehicle windshield.

20. The viewing surface of claim 18, wherein the viewing surface is a window of a building.

21. The viewing surface of claim 18, wherein the viewing surface is an airplane visor.

22. The viewing surface of claim 18, wherein the wavelength transmission blocker is operative to block substantially 100% of light wavelengths up to 400 nm.

23. The viewing surface of claim 18, wherein the wavelength transmission blocker is operative to block about 99% of light between 400 nm and 420 nm and about 20% of light at 510 nm.

24. The viewing surface of claim 18, wherein the wavelength transmission blocker is operative to block a gradually reduced percentage of light wavelengths between 400 nm to 510 nm.

25. The viewing surface of claim 18, wherein the wavelength transmission blocker is operative to block a portion of light wavelengths between 510 nm to 650 nm.

26. The viewing surface of claim 18, wherein the wavelength transmission blocker is operative to block wavelength transmission of wavelengths chosen from a group consisting of ultraviolet A wavelengths, ultraviolet B wavelengths, infrared wavelengths, and combination thereof.

27. The viewing surface of claim 18, wherein the wavelength transmission blocker is a tint composition disposed exteriorly upon the viewing surface.

28. The viewing surface of claim 18, wherein the wavelength transmission blocker is a tint composition disposed interiorly within the viewing surface.

29. A semitransparent viewing surface, comprising a wavelength transmission blocker being sized and configured to block predetermined percentages of light transmission at selective wavelengths, wherein the predetermined percentages being:
substantially 100% at wavelengths up to 400 nm; and
gradually reduced from about 99% at wavelength of 420 nm to about 80% at wavelength of 510 nm.

30. The viewing surface of claim 29, wherein the viewing surface is a vehicle windshield.

31. The viewing surface of claim 29, wherein the viewing surface is a window of a building.

32. The viewing surface of claim 29, wherein the viewing surface is an airplane visor.

33. The viewing surface of claim 29, wherein the wavelength transmission blocker includes a lutein assimilated therein.

34. The viewing surface of claim 29, wherein the predetermined percentages are between 80% to 70% at wavelengths of 510 nm and 650 nm.

35. The viewing surface of claim 29, wherein the wavelength transmission blocker is operative to block ultraviolet A wavelengths, ultraviolet B wavelengths, infrared wavelengths, and combinations thereof.

36. The viewing surface of claim 29, wherein the wavelength transmission blocker is a tint composition disposed exteriorly upon the viewing surface.

37. The viewing surface of claim 29, wherein the wavelength transmission blocker is a tint composition disposed interiorly within the viewing surface.

* * * * *